United States Patent
Druilhe et al.

(10) Patent No.: US 6,472,519 B1
(45) Date of Patent: Oct. 29, 2002

(54) PLASMODIUM FALCIPARUM ANTIGENS INDUCING PROTECTIVE ANTIBODIES

(75) Inventors: Pierre Druilhe, Paris (FR); Hasnaq Bouharoun-Tayoun, Zgharta (LB); Claude Oeuvray, Paris (FR)

(73) Assignee: Institut Pasteur, Paris (FR)

(*) Notice: Subject to any disclaimer, the term of this patent is extended or adjusted under 35 U.S.C. 154(b) by 0 days.

(21) Appl. No.: 09/356,497

(22) Filed: Jul. 19, 1999

Related U.S. Application Data

(62) Division of application No. 08/416,711, filed as application No. PCT/FR93/01024 on Oct. 18, 1993, now Pat. No. 6,017,538.

(30) Foreign Application Priority Data

Oct. 19, 1992 (FR) ............................................. 92/12488

(51) Int. Cl.[7] .................. C07H 21/04; C07H 21/02; C12P 21/06; C12P 21/04; C12N 15/00
(52) U.S. Cl. .................. 536/23.7; 536/24.1; 536/23.1; 536/23.5; 536/24.32; 435/69.1; 435/69.3; 435/69.7; 435/320.1; 435/70.1; 435/70.2; 435/71.1; 435/71.2; 435/235.1
(58) Field of Search ............................. 536/24.1, 23.1, 536/23.5, 23.7, 24.32; 435/69.1, 69.3, 320.1, 69.7, 70.1, 70.2, 71.1, 71.2, 235.1

(56) References Cited

U.S. PATENT DOCUMENTS

| | | | |
|---|---|---|---|
| 4,632,909 A | | 12/1986 | Carter et al. |
| 4,722,840 A | | 2/1988 | Valenzuela et al. |
| 4,835,259 A | | 5/1989 | Resse et al. |
| 4,957,738 A | | 9/1990 | Patarroyo |
| 4,978,621 A | * | 12/1990 | Ardeshir et al. |
| 5,032,397 A | | 7/1991 | Duboise et al. |
| 5,112,749 A | | 5/1992 | Brey et al. |
| 5,225,534 A | | 7/1993 | Certa |
| 5,376,370 A | | 12/1994 | Siddiqui |
| 5,585,268 A | | 12/1996 | Knapp et al. |
| 5,589,343 A | | 12/1996 | Marchand et al. |
| 5,599,542 A | | 2/1997 | Marchand et al. |
| 5,602,031 A | | 2/1997 | Marchand et al. |
| 5,690,941 A | * | 11/1997 | Druilhe et al. |
| 5,720,959 A | | 2/1998 | Holder et al. |
| 5,928,901 A | * | 7/1999 | Marchand et al. |
| 5,993,823 A | * | 11/1999 | Boutillon et al. ......... 424/184.1 |
| 6,017,538 A | * | 1/2000 | Druilhe et al. |
| 6,100,067 A | * | 8/2000 | Druilhe et al. |
| 6,191,270 B1 | * | 2/2001 | Druilhe et al. |

FOREIGN PATENT DOCUMENTS

| | | | |
|---|---|---|---|
| WO | WO 88/00595 | | 1/1988 |
| WO | WO 90/02752 | | 3/1990 |
| WO | WO 92/02549 | | 2/1992 |
| WO | WO 9409140 | * | 4/1994 |

OTHER PUBLICATIONS

Cooper et al, Parasitology Today, 1993, 9/2:50–54 Merozoite Surface Antigen–1 of Plasmodium.*
Ramasamy et al, Parasite Immnology, 1999, 21:397–407 Antibodies to a merozoite surface protein promote multiple invasion of red blood cells by malaria parasites.*
Khusmith et al, Trans. Royal Soc. Trop. Med. & Hyg. 76/3:423–424, 1982.*
Yang etal, Vaccine, 15/12–13:1303–1313, 1997.*
Dong etal, Int. J. Parasitology 31:57–62, 2001.*
Sauzet et al, Infection & Immunity 69/2:1202–1206, 2001.*
DaSilveira etal, Infection & Immunity 67/11:5906–5916, 1999.*
Rzepczyk etal Infection & Immunity 65/3:1098–1100, 1997.*
Oeuvray etal Infection & Immunity 68/5:2617–2620, 2000.*
Huber etal Mol. Biochem. Parasitol. 87:231–234, 1997.*
Okenu etal, Mol. Biochem. Parasitol 109:185–188, 2000.*
McCall etal, Mol. Biochem. Parasitol 90:21–31, 1997.*
Benjamin et al, Mol. Biochem. Parasitol 104:147–156, 1999.*
Ramasamy etal, BBA, 1453:1–13, 1999.*
Smythe etal, PNAS, 88:1751–1755, 1991.*
Benzaquen–Geffin etal, Infection & Immunity 55/2:342–51, 1987.*
Pye etal Infection & Immunity 59/7:2403–2411, 1991.*
Fenton etal Mol & Biochem. Parasitology 34:79–86, 1989.*
Holder etal, Parasitology, 97:373–382, 1988.*
Burns etal J. Immunology 143:2670–2676, 1989.*
Cheung etal, PNAS, 83:8328–8332, 1986.*
Oeuvray et al, Mem. Inst. Oswaldo Cruz, Riode Janeiro 89/11:77–80, 1994.
Khusmith et al, Bull. Soc. Path. E4, 76:137–145, 1983.
Barale et al, Inf. 7 Imm. 65(8):3003–3010, Aug. 1997.
Druilhe et al, Inf. & Imm. 55(4): 888–891, Apr. 1987.
Khusmith et al, Trans. Roy. Soc. Trop. Med.&Hyg. 76(3):423–424, 1982.
Fenton et al, 1991, Mol. & Cell. Biol. 11(2):963–71.
Snewin et al, 1991, Mol. & Biomed. Parasitol, 49:265–276.
Saul et al, 1992, J. Immunol., 148(1):208–211.

(List continued on next page.)

Primary Examiner—Nita Minnifield
(74) Attorney, Agent, or Firm—Oblon, Spivak, McClelland, Maier & Neustadt, P.C.

(57) ABSTRACT

A molecule, protein or peptide characterized in that it is recognized by cytophilic antibodies from individuals who are immune to infection by Plasmodia, and recognized by non-cytophilic antibodies from individuals who are vulnerable to infection by Plasmodiae. Said antibodies are capable of blocking the erythrocytic phase of the parasite by co-operating with accessory cells such as monocytes.

21 Claims, 1 Drawing Sheet

OTHER PUBLICATIONS

Taylor et al, 1995, Inf & Imm. 63(11):4382–88.
Rutgers et al, 1988, Bio/Technology. 6:1065–70.
Oeuvary et al, 1994, Blood, 84(5):1594–1502.
Marshall et al, 1991, Mol. & Biomed. Parasitol, 45:349–51.
McBride et al, 1985, J. Exp. Med. 161:160–180.
Flint et al, 1986, Vaccines 86, pp. 175–179, Ed. Brown et al.
Perkins et al, 1986, Vaccines 86, pp. 157–160.
Von Brunn et al, 1991, Vaccine 9:477–484.
Nester et al, 1996, Lancet, 348:701–707.
Sherwood et al, 1996, Vaccine, 14(8):817–827.
1992, Current Opin. Immunol. 4:432–441 Romero P: Malaria vaccines. Curr. Opin. Immunol 4:432, 1992.
Butcher, 1989, Parasitol, 98:315–327.
Cox 1991, Tibtech, 9:389–394.
Bowie et al, 1990, Science, 247:1306–1310.
Houghten et al ,1986, Vaccines 86, pp. 21–25.
Bixler et al., 1987, In Synthetic Vaccines vol. 1:39–71.

* cited by examiner

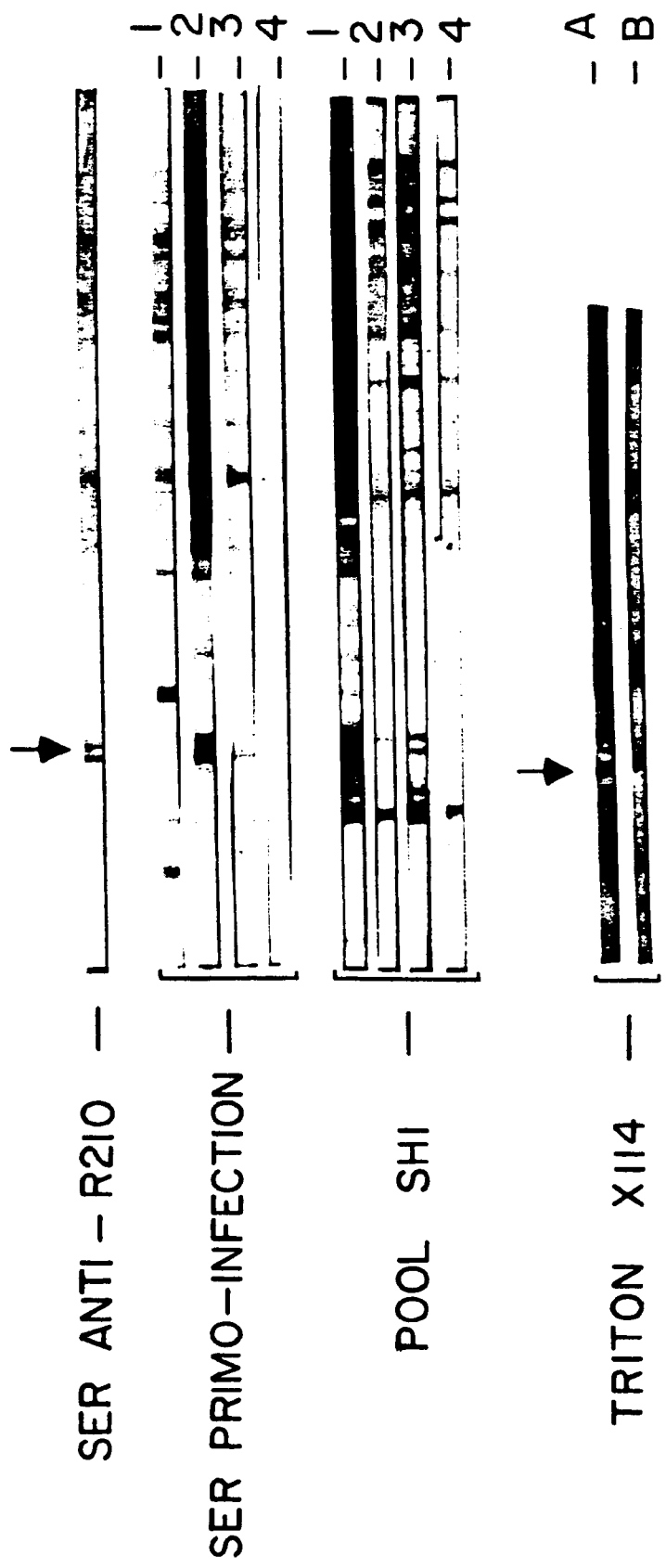

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 64 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

His Glu Arg Ala Lys Asn Ala Tyr Gln Lys Ala Asn Gln Ala Val Leu
1               5                   10                  15

Lys Ala Lys Glu Ala Ser Ser Tyr Asp Tyr Ile Leu Gly Trp Glu Phe
            20                  25                  30

Gly Gly Gly Val Pro Glu His Lys Lys Glu Glu Asn Met Leu Ser His
        35                  40                  45

Leu Tyr Val Ser Ser Lys Asp Lys Glu Asn Ile Ser Lys Glu Asn Glu
    50                  55                  60

(2) INFORMATION FOR SEQ ID NO: 2:

(i) SEQUENCE CHARACTERISTICS:
      (A) LENGTH: 23 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 2:

His Glu Arg Ala Lys Asn Ala Tyr Gln Lys Ala Asn Gln Ala Val Leu
1               5                   10                  15

Lys Glu Ala Ser Ser Tyr Asp
            20

(2) INFORMATION FOR SEQ ID NO: 3:

(i) SEQUENCE CHARACTERISTICS:
      (A) LENGTH: 27 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 3:

Ala Lys Glu Ala Ser Ser Tyr Asp Tyr Ile Leu Gly Trp Glu Phe Gly
1               5                   10                  15

Gly Gly Val Pro Glu His Lys Lys Glu Glu Asn 20                25

(2) INFORMATION FOR SEQ ID NO: 4:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Pro Glu His Lys Lys Glu Glu Asn Met Leu Ser His Leu Tyr Val Ser
1               5                   10                  15

Ser Lys Asp Lys Glu Asn Ile Ser Lys Glu Asn Glu
            20                  25

(2) INFORMATION FOR SEQ ID NO: 5:

(i) SEQUENCE CHARACTERISTICS:
        (A) LENGTH: 192 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 5:

CATGAAAGGG CAAAAAATGC TTATCAAAAA GCAAACCAAG CTGTTTTAAA AGCAAAAGAA        60

GCTTCTAGTT ATGATTATAT TTTAGGTTGG GAATTTGGAG GAGGCGTTCC AGAACACAAA       120

AAAGAAGAAA ATATGTTATC ACATTTATAT GTTTCTTCAA AGGATAAGGA AAATATATCT      180

AAGGAAAATG AG                                                           192

(2) INFORMATION FOR SEQ ID NO: 6:

(i) SEQUENCE CHARACTERISTICS:
        (A) LENGTH: 75 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 6:

CATGAAAAGG CAAAAAATGC TTATCAAAAA GCAAACCAAG CTGTTTTAAA AGCAAAAGAA        60

GCTTCTAGTT ATGAT                                                        75

(2) INFORMATION FOR SEQ ID NO: 7:

(i) SEQUENCE CHARACTERISTICS:
        (A) LENGTH: 81 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 7:

GCAAAAGAAG CTTCTAGTTA TGATTATATT TTAGGTTGGG AATTTGGAGG AGGCGTTCCA        60

GAACACAAAA AAGAAGAAAA T                                                 81

(2) INFORMATION FOR SEQ ID NO: 8:

-continued

```
     (i) SEQUENCE CHARACTERISTICS:
          (A) LENGTH: 84 base pairs
          (B) TYPE: nucleic acid
          (C) STRANDEDNESS: double
          (D) TOPOLOGY: linear (ii) MOLECULE TYPE: DNA (genomic)

(xi) SEQUENCE DESCRIPTION: SEQ ID NO: 8:

CCAGAACACA AAAAAGAAGA AAATATGTTA TCACATTTAT ATGTTTCTTC AAAGGATAAG      60

GAAAATATAT CTAAGGAAAA TGAG                                             84

(2) INFORMATION FOR SEQ ID NO: 9:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "SYNTHETIC DNA PRIMER"

(xi) SEQUENCE DESCRIPTION: SEQ ID NO: 9:

GAAAGGGCAA AAAATGCTTA T                                                21

(2) INFORMATION FOR SEQ ID NO: 10:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "SYNTHETIC DNA PRIMER"

(xi) SEQUENCE DESCRIPTION: SEQ ID NO: 10:

TAAAAGGAAT CTATATAAAA G                                                21
```

PLASMODIUM FALCIPARUM ANTIGENS INDUCING PROTECTIVE ANTIBODIES

This application is a Division of application Ser. No. 08/416,711, filed Oct. 8, 1993, now U.S. Pat. No. 6,017,538, which is in turn a national phase of International Application PCT/FR93/01024, filed Oct. 18, 1993, which in turn claims foreign priority to the French Application 9212488, filed Oct. 19, 1992.

BACKGROUND OF THE INVENTION

The object of the present invention is novel preparations for a broad-spectrum antiplasmodial vaccine.

The object of the invention is also a vaccinating antigen of *Plasmodium falciparum* capable of inducing a resistance to the parasite which reproduces that observed in the mechanism of protective immunity or premunition.

The object of the invention is also preparations of monoclonal or poyclonal antibodies or chimeric fragments obtained from these antibodies specific for these antigens and likely to form part of a composition for passive immunotherapy.

Finally, the object of the invention is a kit permitting the in vitro diagnosis of the infection of an individual by a broad spectrum of plasmodial strains.

DESCRIPTION OF THE RELATED ART

The parasites responsible for malaria in man, including in particular *Plasmodium falciparum* or *Plasmodium vivax* to mention only the principal ones, exhibit different morphologies in the human host and express different antigens as a function of their localization in the organism of the infected host. The morphological and antigenic differences of these parasites during their life cycle in man enable at least four distinct stages d development to be defined.

The very first stage of development of the parasite in man corresponds to the sporozoite form introduced into the blood of the host by bites of insect vectors of the parasite. The second stage corresponds to the passage of the parasite into the liver and to the infection of the hepatic cells in which the parasites develop to form the hepatic schizonts which, when they are mature (for example in the case of *P. falciparum* on the 6th day after penetration of the sporozoite) release hepatic merozoites by bursting. The third stage is characterized by the infection of the blood erythrocytes by the asexual forms (merozoites) of the parasite; this erythrocytic stage of development corresponds to the pathogenic phase of the disease. The fourth stage corresponds to the formation of the forms with sexual potential (or gametocytes) which will become extracellular sexual forms or gametes in the mosquito.

It is known that very many studies have been undertaken to isolate from strains of parasites which infect a human host polypeptide fractions to permit the in vitro diagnosis of malaria by the detection of the corresponding antibodies, on the one hand, and to attempt to vaccinate against malaria, on the other.

In 1976 the maintenance (so long-awaited) of *P. falciparum* in continuous culture in human RBC was accomplished (Trager and Jensen, Science 1976, 193: 673; Haynes et al., 1976). This achievement facilitated access to the parasite considerably and stimulated research which since then has experienced a rapid development. Efforts have been oriented mainly towards the development of a vaccine which in future will be necessary to control malaria whose incidence is becoming worse in as much as resistance of the parasite to drugs is spreading in different parts of the world.

In the search for a vaccine against the agent responsible for malaria, biologists are confronted with various problems not observed with other infectious agents such as viruses or bacteria. Of these special difficulties with the parasite we will mention principally:

The complexity Of the biological cycle of the plasmodium taking place in two different hosts, the mosquito and man, undergoing sexual reproduction in the one and 2 different phases of asexual multiplication in the other. Thus 2 stages take place in man differing in their site of development (the liver and the blood circulation) and in their antigenic specificities.

The antigenic diversity of the parasite Since 1983 the plasmodial antigens have been cloned and their nucleotide and protein sequences have been analyzed. This detailed study shows that more than 50% of the known antigens exhibit a high degree of polymorphism from one strain to another.

At the immunological level, the host-parasite relationship is very subtle As has already been mentioned, for a given parasite it is very different depending on the host in which it evolves. This leads to the difficulty of interpretation of the results obtained in the experimental models.

Furthermore, in the natural infection sterilizing immunity is never seen like that observed for example in viroses. However, there is no doubt that an acquired immunity exists but it is partial and labile.

Thus the complexity and the diversity of the parasite as well as the unusual nature of the immune response that it elicits are the major reasons for the absence of an antimalarial vaccine at present.

The research approach most often taken in the development of a vaccine against malaria due to *P. falciparum* hence consists of the identification (on the basis of the information cited above) of a potential candidate, and then the evaluation of its value either in vitro by testing the specific antibodies in the inhibition of the growth of the parasite or of certain of its properties (cytoadhesion, rosette formation . . . ), or in vivo by the immunization of monkeys often with the complete Freund adjuvant. The present situation may thus be summed up as the existence of a large number of potential candidates characterized by their biochemical properties, their nucleotide and protein sequences, their degree of polymorphism, their localization on the parasite etc. Nevertheless, the researchers dispose of limited means for assessing the value of their candidates: 1) in vitro tests implicating mechanisms of action of antibodies whose validity in vivo is poorly documented, 2) vaccinations of non-human primates, and hence the evaluation of the effect of a vaccine on an experimental infection is based an parasitological and clinical parameters and particularly the type of immunity which may be induced which are very different from those of the natural infection in man.

The strict specificity of the host-parasite relationship leads under natural conditions to the opposite of what is ed in the animal models, to an equilibrium in which the parasite survives by inducing in its natural host a non-sterilizing immunity. The chronic nature of the parasitic infection suggests that the majority of the molecular components of the parasite are selected so as to protect the micro-organism against the immune defences of the individual infected, and do so by means of escape which are very varied but specifically adapted to the natural host. In the experimental host, the poorly adapted parasite defends itself less well against the immune system and protection against a single treated infection is easy to obtain, and vaccination is still easier to obtain.

Gordon-Thomson, Immunity in Malaria, Trans. Ray.Soc. Trop. Med. Hyg. XXVI (6) 483–514) dearly concluded that immunity against *P. falciparum* can only be acquired in the regions where transmission is essentially continuous year after year This "tolerance" to parasitism requires at the individual level an uninterrupted infection for about 15 years, sometimes 20 years and up to 26 years in a study conducted in Panama An immunity associated with a latent infection necessary for the maintenance of the protection results from this. Sergent (1935). Institut Pasteur d'Algerie Archives, 3:279 suggested the term "premunition" to define this "particular state or resistance contemporaneous with the infection and ceasing with it".

Thus the immunity (or premunition) against *P. falciparum* acquired by man in a holo- or hyperendemic zone is characterized by:

a very long delay prior to its installation (15 to 20 years of infection)

its incapacity to abolish the infection, it is a non-sterilizing immunity.

its lability. In the absence of any reinfection (during more than one year), the premonition is lost and the subject again becomes susceptible to the disease if subject to a new infection.

The indications in favour of humoral immunity in acquired protection against malaria cone from the first attempts at passive transfer of serum from an individual in the "chronic" phase who had reached a state of premonition (i.e. showing circulating parasites in small numbers without any clinical manifestation) to a subject in the acute phase. The condition of this latter is found to be improved subsequent to this passive transfer (Sotiriades 1917, Attempts at serotherapy in malaria Greek Med. XIX: 27–28).

The role of antibodies in premunition is demonstrated by several experiments of passive transfer carried out at the beginning of the 1960s. The transfer of IgG purified from hyperimmune African adult serum cures child victims of an acute infection by appreciably reducing their parasitemia (Cohen et al., 1971, Trans, Roy. Soc. Trop. Med. Hyg. 65 (2): 125–135; McGregor et al., 1964, the passive transfer of human material immunity, Am. J. Trop. Med. Hyg. 13: 237–239). The newborn are protected up to the third month of their life as a result of maternal antibodies; this is proved by the beneficial effect of the IgG of the umbilical card transferred to children suffering from an acute attack due to *P. falciparum* (Edozien et al., 1962).

The development of immunity and its efficacy in the protection of man against *P. falciparum* nonetheless proves the existence of parasite molecules which are the targets of an effective immune defence.

Recent experiments have made it possible to show that a) the G immunoglobulins (IgG) of immune African adults are protective by passive transfer in man infected with malaria (Sabchareon et al., Amer. J. of Trop. Med. and Hyg., vol. 45, No.3, Sept. 1991, 297–308), b) that, contrary to what is believed to be established, these antibodies are incapable of directly inhibiting the invasion of red cells by the parasites; on the other hand, they act by an antibody-dependent cellular inhibition mechanism (ADCI) in which the monocyte plays the role of effector cell (Bouharoun-Tayoun et al., J. Exp. Med, vol. 172, Dec.1990 pp. 1633–1641; S. KHusmith et al., 1983, Inf. Imm. 41 (1): 219 and F. Lunel et al., 1989 Inf. Imm. 57: 2043), c) This mechanism necessarily implicates cytophilic antibodies, i.e. those capable of binding to the monocyte through their Fc receptor; in fact, there has been observed in the serum of protected subjects a prevalence of cytophilic isotypes IgG1 and IgG3 and in non-protected subjects a preponderance of non-cytophilic classes, IgG2 and/or IgM (H. BOUHAROUN-TAYOUN et al., 1992, Infection and Immunity, pp. 1473–1481).

SUMMARY OF THE INVENTION

One of the objectives of the present invention is the development of polypeptide for the vaccination of humans against malaria, polypeptides which are a target of the defence mechanisms prevailing in the individuals having acquired an immunity by prolonged exposure to the parasite and their use in a vaccine by attempting to reproduce the same state of resistance by the same mechanism as that observed in the establishment of protective immunity.

The object of the invention is also the use of these same polypeptide in an in vitro diagnostic kit for the infection in man by a broad spectrum of plasmodial strains.

The invention relates more particularly to molecules or peptide or polypeptide compositions characterized by the presence in their structure of one or more peptide sequences bearing one or more epitopes characteristic of a protein recognized by antibodies of the cytophilic class, i.e. capable of binding to the for receptors of the monocytes through their Fc region, and not recognized by non-cytophilic antibodies and of promoting an antibody-dependent cytotoxicity mechanism (ADCI).

A protein of the invention is a merozoite surface protein of 48,000 molecular weight (48 kD), exhibiting the properties given below.

The polypeptides of the invention were obtained by the identification of a part of this protein of 48.000 daltons molecular weight (48 kD) Of the merozoite surface, this identification being described below, the biochemical and immunological characterization of the 48 kD protein, the screening of a genomic library of the plasmodium for its capacity to inhibit the coupling of a specific monoclonal antibody of the IgM type which has the special characteristic of blocking the ADCI-type reaction ("antibody-dependent cellular inhibition") induced by the specific IgG of the plasma of the subjects protected by premunition the characterization of the proteins synthesized by the clones selected, the sequencing of the insert of the clone selected the search for the functional effect of the antibodies corresponding to this protein in the tests described.

BRIEF DESCRIPTION OF THE DRAWING

FIG. 1 shows the detection of the parasite protein of 48,000 (indicated by the arrows) by immunoblot. The reactivity of the serum of mice immunized with DG210 is studied in immunotransfer on the antigens of the blood stages of *P. falciparum* extracted into SDS (anti-R210 sera) or into Triton-X114 detergent phase (A) and aqueous phase (B). The reactivity of the human sera is studied on the SDS extracts by revealing the isotypes IgG1 (1), IgG2 (2), IgG3 (3) and IgG4 (4). HIS: hyperimmune serum.

DETAILED DESCRIPTION OF THE PREFERRED EMBODIMENTS

The value of the proteins and peptides of the invention and the strategy used to obtain them are made explicit in the description below.

Selection Strategy for the Proteins and Peptides

1—In *Infection and Immunity* (pp1473–1481, April 1992), the authors study the isotypic distribution of individuals infected by the plasmodium exhibiting various immunological states In this way they have shown that the unprotected subjects have an anti-plasmodial plasma antibody composition very much in favour of the non-cytophilic isotypes, namely IgG2 and IgM. In certain cases, this equilibrium relates to the antibodies against all of the malarial polypeptides detectable by Western blot (procedure described in Molecular Cloning 1989, Sambrook et al.) whereas in other cases it was possible to demonstrate IgG2 specific for a given polypeptide, often a polypeptide of 48 kD appearing in certain isolates in the form of a dimer or a polypeptide of 80–100 kD. On the other hand, the polypeptide of 48 kD is always recognized by the cytophilic isotypes IgG1 and IgG3 in adults who have acquired resistance to the disease, or a state of premunition.

2—It has often been observed in competition experiments that the total purified Ig of unprotected individuals block the ADCI reaction (see description below) induced by the IgG of resistant subjects This result suggests that the unprotected subjects have developed antibodies directed against the same epitopes as those which are recognized by the protecting antibodies, but owing to the non-cytophilic character of the IgG2 or IgM derived from the unprotected subjects, these antibodies are incapable of promoting the destructive effect of the monocytes but, on the other hand, are capable of entering into competition with antibodies effective in ADCI When such a competitive effect was identified by using human sera in which the antibodies against the 48 kD protein were predominantly of the IgG2 isotype, that clearly demonstrates the significance of this 48 kD protein.

The ADCI test has already been described in the publication cited above (H. BOUHAROUN-TAYOUN et al, Khusmith et al., Lunel et al.). Briefly, it is a test of the inhibition of growth of the parasite by the IgG in the presence of monocytes. The monocytes are isolated by adhesion to the plastic (in a 96-wells plate) from the fraction of mononucleated cells of the peripheral blood of a normal donor. A synchronous culture of *P. falciparum* at 0.5% parasitemia in mature form is added to the monocytes in a monocytes/ red cells ratio of about 1/200. The hematocrit being 2%, the medium is supplemented by the serum or the IgG to be tested. The reference cultures consist of parasites in the presence of normal IgG, parasites in the presence of manocytes and normal IgG, parasites in the presence of the IgG to be tested.

Depending on the case, the culture will be stopped after 24, 48, 72 or 96 hours. In the last two cases, 50 microliters of the culture medium are added. The final parasitemia in each of the wells is estimated by counting 10.000 red cells on stained smears. The results are presented in the form of a specific growth inhibition index (SI) expressedas a percentage and calculated as follows, taking into consideration of the possible inhibitory effect on the monocyte culture and/Cr antibodie alone:

$$SI = \frac{1 - \% \text{ parasitemia culture} + \text{IgG test}/ \% \text{ parasitemia monocytes} + \text{IgG test}}{\% \text{ parasitemia monocytes} + \text{IgG}/\% \text{ parasitemia culture} + \text{IgG}}$$

This selection strategy for a potentially vaccinating protein of 48 kD according to the recognition criteria by cytophilic antibodies in protected subjects and non-cytophilic antibodies in unprotected subjects as well as by their capacity to induce antibodies capable of cooperating with monocytes in ADCI have led us to select this 48 kD protein or peptides representing the epitopic regions of this protein as potentially very useful candidates for inducing the protective immunological effect against infections of *P. falciparum* in patients.

The invention also relates particularly to molecules or peptide or polypeptide compositions characterized by the presence in their structure of one or more peptide sequences bearing one or more epitopes characteristic of the protein and meeting the three criteria:

recognition by antibodies of the cytophilic class in protected subjects and non-cytophilic in unprotected subjects, their capacity to induce antibodies capable of cooperating with monocytes in ADCI, their slight or non-existent polymorphic character in as much as the protective immunity can be exercised with respect to a large number of strains.

The molecules of the invention are all at the molecules bearing epitopes, recognized by antibodies recognizing epitopes borne by the 48 kD protein of the merozoite surface.

A polypeptide composition according to the invention is characterized by the presence of a sequence of 64 amino acids or a derivative sequence possessing the same antigenic properties, and an example of which is given in the following formula I (SEQ ID NO:1):

```
his glu arg ala lys asn ala tyr gln lys ala asn gln ala val leu lys ala lys glu ala ser ser tyr asp tyr ile leu gly trp glu phe gly gly gly val pro glu his lys lys glu glu asn met leu ser his leu tyr val ser ser lys asp lys glu asn ile ser lys glu asn glu
```

The invention relates primarily to synthetic monomeric peptides comprising a unique peptide sequence of 64 amino acids corresponding respectively to the formula indicated above and whose terminal amino adds possess free amino and carboxylic extremities respectively, or oligomers containing in particular multiples of any one of the above-mentioned peptide sequence.

It is obvious that the free reactive functions which some amino acids forming part of the constitution of the molecules according to the invention are likely to possess, in particular the free carboxyl groups borne by the Glu residues and by the C-terminal amino acid, on the one hand, and/or the free groups bone by the N-terminal amino acid or by amino acids in the interior of the peptide chain, for example Lys, on the other, may be modified provided that this modification does not lead to a modification of the antigenic, possibly immunogenic properties of the entire molecule. The molecules thus modified are naturally included in the framework of the protection given to the invention by the Claims. These carboxylic functions are possibly acylated or esterified.

Other modifications are also included in the framework of the invention. In particular, amine or ester functions, or both at once, of the terminal amino acids may be themselves be engaged in linkages with other amino acids For example, the N-terminal amino acid may be linked to a sequence comprising one or more amino acids corresponding to a part of the C-terminal region of another peptide conforming to the definition which has been given to it above, or vice versa.

It will be obvious that any peptide sequence derived from the modification of the peptide sequence of 64 amino acids by substitution and/or by addition and/or deletion of one or more amino acids is included in the framework of the protection given to the invention by the Claims, provided that this modification does not impair the antigenic or immunogenic properties of the pciypeptide, in particular when these immunogenic properties have been reinforced adequately, for example by combination of this polypeptide with a suitable immunological adjuvant (for example, a muramylpeptide) or by coupling with a carrier molecule of higher molecular weight (for example a serum albumin or a polylysine ) or a toxin of the tetanic type or another antigen of *P. falciparum*.

The invention relates more generally to any molecule characterized by the presence in its structure of One or more peptide sequences exhibiting immunological cross-reactions with the peptide sequence corresponding to the preceding formula with respect to the antibodies inducible by these latter in vivo.

The invention also relates to any peptide whose structure is derived from the preceding one and in particular to one of the three peptides of formula II, III, IV (SEQ ID NO:2–4).

```
his glu arg ala lys asn ala tyr gln lys ala asn   II
gln ala val leu lys glu ala ser ser tyr asp
ala lys glu ala ser ser tyr asp tyr ile leu gly  III
trp glu phe gly gly gly val pro glu his lys lys
glu glu asn
pro glu his lys lys glu glu asn met leu ser his   IV
leu tyr val ser ser lys asp lys glu asn ile ser
lys glu asn glu
```

As in the case of the first peptide defined above, the different peptides which have just be named may be modified without being excluded from the framework of the invention provided that these structural modifications do not lead to major changes in their antigenic properties.

The peptides according to the invention may be prepared by the standard procedures used in the field of peptide synthesis. This synthesis may be carried out in homogeneous solution or on a solid phase.

For example, recourse may be had to the procedure of synthesis in a homogeneous solution described by HOUBENWEYL in the monograph entitled "Methoden der Organischen Chemie" (Methods in Organic Chemistry) edited by E. Wunsch, vol. 15-I and II, THIEME, Stuttgart 1974.

This method of synthesis consists of successively condensing in the required order the successive amino acids or of condensing peptide fragments previously formed already containing several amino acids in the required order, it being understood that care will be taken to protect temporarily all of the reactive functions borne by these amino acids or peptide fragments, with the exception of those amino and carboxyl functions which are necessarily implicated in the formation of the peptide bonds, in particular after activation of the said carboxyl functions, according to the methods well-known in peptide synthesis, As an alternative, it is possible to have recourse to coupling reactions involving standard coupling reagents of the carbodiimide type, such as for example 1-ethyl-3-(3-dimethyl-amino-propyl)-carbodiimide.

When the aminoacyl residue to be coupled possesses an additional acidic function (in particular in the case of glutamic acid), these functions are protected, for example, by means of t-butyl ester groups.

In the case of stepwise synthesis, amino acid by amino acid, the synthesis starts preferably by the condensation to the C-terminal amino acid of the next amino acid in the desired sequence and so on, one at a time, the other amino acids selected in appropriate sequence, the synthesis being completed with the attachment of the N-terminal amino acid. According to another preferred procedure of the invention recourse is had to the procedure described by R. D. MERRIFIELD in the article entitled "Solid phase peptide synthesis" (J. Am. Soc, 45: 2149–2154).

In order to synthesize a peptide chain according to the MERRIFIELD procedure, the first amino acid, the C-terminal amino acid of the chain, is attached to a very porous resin polymer. This amino acid is bound to the resin through the intermediary of its carboxyl group and its amino function is protected, for example, by the t-butoxycarbonyl group.

When the first, C-terminal amino add has thus been attached to the resin, the protecting group of the amino function is removed by washing the resin with acid.

In the case in which the protecting group of the amine function is the t-butoxycarbonyl group, it may be removed by treatment of the resin with trifluoroacetic acid.

The second amino acid is then coupled to the deprotected amine function of the first C-terminal amino acid to furnish the second aminoacyl residue of the desired sequence, counting from the C-terminus. Preferably, the carboxyl function of this second amino add is activated for example by means of dicyclohexyl-carbodiimide and the amine function is protected, for example by means of the t-butoxycarbonyl group.

The first part of the desired peptide chain is thus obtained, which contains two amino acids and the terminal amino function of which is protected. As previously, the amine function is deprotected and it is then possible to proceed to the attachment of the third aminoacyl residue under conditions analogous to those for the addition of the second, penultimate C-terminal amino acid.

In this way, the amino acids which will constitute the peptide chain are added one after the other to the previously deprotected amine group of the portion of the peptide chain already formed which is attached to the resin.

When the desired peptide chain has been assembled in its entirety, the protecting groups of the different side chains of the amino acids constituting the peptide chain are removed and the peptide is cleaved from the resin, for example with the aid of hydrogen fluoride.

The invention also relates to water-soluble oligomers of the monomeric peptides indicated above.

The oligomerization may cause an increase in the immunogenicity of the monomeric peptides according to the invention. Without such numerical values being considered as limiting, it should nonetheless be mentioned that these oligomers may contain, for example, from 2 to 10 monomeric units.

The monomeric units forming part of this oligomer are either constituted by the polypeptide of sequence I or by the polypeptides of sequence I, III or IV.

In order to carry out the oligomerization, recourse may be had to any polymerization procedure currently used in the field of peptides, this polymerization being conducted until an oligomer or polymer is obtained which contains the required number of monomeric motifs for the acquisition of the desired immunogenicity.

One method of oligomerization of polymerization of the monomer consists in the reaction of the latter with a cross-linking agent such as glutaraldehyde.

It is also possible to have recourse to other methods of oligomerization or coupling, for example to that making use of the successive coupling of monomeric units through the intermediary of their terminal carboxyl and amino functions in the presence of homo- or hetero-bifunctional coupling agents.

For the production of molecules containing one or more motifs of 64 amino adds such as defined above it is also possible to have recourse to genetic engineering procedures making use of micro-organisms transformed by a specific nucleic acid comprising corresponding suitable nucleotide sequences.

Consequently, the invention also relates to nucleic acids containing one or more of these sequences each comprising 64 triplets of the type indicated above.

The invention also relates to the conjugates obtained by covalent coupling of the peptides according to the invention (or the above-mentioned oligomers) to carrier molecules (natural or synthetic), physiologically acceptable and non-toxic, through the intermediary of complementary reactive groups borne respectively by the carrier molecule and the peptide. Examples of suitable groups are illustrated in what follows:

As examples of carrier molecules or macromolecular supports forming part of the composition of the conjugates according to the invention, mention should be made of naturally occurring proteins such as tetanus toxoid, ovalbumin, serum albumin, hemocyanins, Mention should be made, for example, of polylysine or poly (D-L-alanine)-poly (L-lysine) as examples of synthetic macromolecular supports.

The literature mentions other types of macromolecular supports which can be used and which usually have a molecular weight higher than 20,000.

In order to synthesize the conjugates according to the invention, recourse may be had to known procedures such as that described by FRANTZ and ROBERTSON in Infect. and Immunity, 33, 193–198 (1981) or that described in Applied and Environmental Microbiology, (October 1981), vol. 42, No. 4, 611–614 by P. E. KAUFFMAN by using the peptide and the appropriate carrier molecule.

In practice, the following compounds, cited in a non-limiting manner, are advantageously used as coupling agents: glutaraldehyde, ethyl chloroformate, water-soluble carbodiimides: N-ethyl-N' (3-dimethylamino-propyl) carbodiimide HCl, diisocyanates, bis-diazobenzidine, di- and tri-chloro-s-triazines, cyanogen bromide as will as the coupling agents mentioned in Scand. J. Immunol., (1978), vol. 8, p. 7–23 (AVRAMEAS, TERNYNCK, GUESDON).

It is possible to have recourse to any coupling procedure implicating on the one hand, one or more reactive functions of the peptide and, on the other, one or more reactive functions of the molecular supports. Advantageously, these are carboxyl and amine functions which can give rise to a coupling reaction in the presence of a coupling agent of the type used in the synthesis of proteins, for example, 1-ethyl-3-(3-dimethylamino-propyl)-carbodiimide N-hydroxybenzotriazole, etc. . . . It is also possible to have recourse to glutaraldehyde, in particular when it is required to link together amino groups bone by the peptide and the molecular support, respectively.

A group of preferred molecules according to the invention is constituted of those possessing an alpha helical conformation, this latter reinforcing the antigenic and immunogenic properties of said molecules. Such molecules possessing an alpha helical conformation were demonstrated by circular dichroism in trifluoroethanol or in aqueous solution.

The molecules according to the invention possess antigenic properties characteristic of the 48 kD antigen of the merozoite specific for the erythrocyte stage of the development of P. falciparum and exhibiting the particular characteristics described above.

In fact, as will be more particularly described with the aid of examples of molecules according to the invention in the detailed description which follows, the molecules according to the invention react specifically with the anti-48 kD protein antibodies predominantly of the IgG2 or IgM isotype in the patients sensitive to the infection, and predominantly of the IgG1 or IgG3 isotype in protected subjects.

These molecules according to the invention are capable of triggering in vivo the synthesis of specific immunoglobulins, and are capable of inducing in vivo the neutralization of the merozoite present in the blood, its process in the monocytes and the inactivation of the intraerythrocytic development of P. falciparum subsequent to an interaction between the monocytes and the extra-erythrocytic free parasites or merozoites through the intermediary of a cytophilic antibody by binding of the Fc fragment of the immunoglobulin to the gamma receptor of the monocyte.

FIG. 1 shows the detection of the parasite protein of 48,000 (indicated by the arrows) by immunoblot. The reactivity of the serum of mice immunized with DG210 is studied in immune transfer on the antigens of the blood stages of P. falciparum extracted into SDS (anti-R210 ser) or into Triton-X114 detergent phase (A) and aqueous phase (B). The reactivity of the human sera is studied on the SDS extracts by revealing the isotypes IgG1 (1), IgG2 (2), IgG3 (3) and IgG4 (4). HIS: hyperimmune serum.

EXAMPLE

In the following example as in all of the experiments described in the present description the immunoglobulins of human plasma are obtained by the method described by A SABCHAREON et al., J. Trop. Med. Hyg. 1991, 45 (3): 297). The ADCI test is described above.

In the following example the specific inhibition indices (S.I.) obtained both with sera of mice immunized with the peptide III and with immune human antibodies purified with the aid of an affinity column bearing the peptide III (procedure described in OKAZI et al.) are compared. Both the sera and the antibodies are capable of recognizing the 48 kD protein both in indirect immunofluorescence and in Western blot tests, and do so under the same conditions as previously (IgG2 of sensitive patients and IgG1 or IgG3 of protected patients). Finally, the immunopurified antibodies like the antibodies induced by injection of peptide II into the mouse tested in ADCI tests confirm that they are capable of inducing the inactivation of the parasite by the intermediary of the monocytes.

The following Table I summarizes the results in support of these observations

TABLE 1

| | Antibodies | Specific inhibition index (%) |
|---|---|---|
| Controls (+) | Pshi | 60 |
| | shi1 | 77 |
| | shi2 | 66 |
| Controls (−) | spi | 0 |
| | anti-βgal | −18 |
| Test | anti-DG210 | 45 |
| | anti-DG328 | −13 |
| | anti-DG414 | 4 |
| | anti-210B1 | 72 |
| competitions | B2 | 80 |
| | Pshi + Acm245 | 20 |
| | Pshi + spi | 23 | in which Pshi represents a pool of hyperimmune serum, shi1 and 2 of the hyperimmune sera of two different donors, spi and anti-betagal, controls derived from serum after a first invasion and an anti-betagal control; anti-DG210 are purified antibodies against peptide I, anti-210B (1) are purified human antibodies against peptide III anti-210B (2) are the antibodies induced in the mouse and the anti-R328 and R414 are purified antibodies against peptides derived from other clones.

The specific inhibition index is that measured by the ADCI procedure.

The molecules acording to the invention are hence capable of inducing the synthesis of antibodies of a class capable of cooperating with monocytes.

The proteins and peptides of the invention are not limited to those particularly described above.

The invention relates to all of the natural peptides or poly-peptides obtained by genetic recombination or synthesis which exhibit the same properties of being capable of inducing immune defence mechanisms developed and characteristic of the subjects protected by malaria.

As a result of this feature, the invention relates in particular to epitope of the 48 kD protein different from the polypeptides II, III and IV above In fact, we have been able to show that the immunoglobulins of some individuals read with an epitope of the 48 kD protein in Western blot whereas these same immunoglobulins do not recognize the antigen expressed by the done DG210.

The invention also relates to the poyclonal or monoclonal antibodies exhibiting the characteristic of recognizing the molecules of the invention and of cooperating with the monocytes, and capable of being used in pharmaceutical compositions to protect infected subjects by passive immunotherapy and presenting or being able to present the symptoms of the disease.

The monoclonal antibodies may be produced by the hybridoma technique in accordance with the standard procedures comprising:

the fusion of a myeloma cell with spleen cells of an animal previously immunized with one of the antigens according to the invention, the culture of the hybridomas formed by the fusion of the aforementioned cells and, the selection of those hybridomas capable of foaming monoclonal antibodies recognizing the antigen used for the immunization of the animals.

The animals selected for the immunization may be for example mice.

Of these monoclonal antibodies the cytophilic monoclonal antibodies will be selected advantageously, i.e. those whose Fc fragment is capable of binding to the Fc receptor of the human monocytes.

Another procedure for the production of antibodies may enable human monoclonal antibodies to be formed in vitro. To do this, *B lymphocytes* immortalised with, for example, the Epstein Barr virus are used. These lymphocytes may be taken from a person having been infected by *P. falciparum*. In this case, they make possible the production of monoclonal antibodies against several antigens without having recourse to in vitro stimulation by novel antigens.

Another possibility consists in fusing *B lymphocytes* immortalised as described above with human *B lymphocytes* stimulated in vitro beforehand with an antigen according to the invention against which it is desired to form monoclonal antibodies under culture conditions permitting the stimulation of the lymphocytes.

Reference will advantageously be made to the technique described by Desgranges C. et al. (1987, J. of Virological Methods, vol. 16, p281–292) for the preparation of the human monoclonal antibodies of the invention.

It is also contemplated within the framework of the invention to produce human monoclonal antibodies by genetic recombination by carrying out an in vitro transfection of the gene coding for the variable part of the antibody into vectors infecting bacteria under conditions permitting the expression of a human immunoglobulin.

Finally, the present invention relates to any type of monoclonal antibody, chimeric or hybrid, or even any fragment of poyclonal or monoclonal antibody of the Fab or Fab'2 type, and exhibiting the same affinity characteristics for the epitopes of the 48 kD protein or the peptides I, II and III, IV below.

Preferred monoclonal antibodies according to the invention are human antibodies of class IgG1 or IgG3, or antibodies obtained in animals and having cytophilic properties in man, directed against one or more of the antigens whose sequence was described above.

The invention also relates to a procedure for monitoring the vaccination of the patient against infection with *P. falciparum*, starting from a biological sample such as blood, characterized in that it comprises:

the placing of the biological sample likely to contain protective antibodies against *P. falciparum* in contact with at least one antigen according to the invention, the detection of the antigen-antibody reaction.

For carrying out this in vitro detection method the antigens according to the invention are advantageously labelled with the aid of a radioactive marker, an enzymatic or fluorescent label or even a physical type of marker.

The invention also relates to kits for the in vitro detection of the presence of antibodies directed against the antigens of the invention, characterized in that they contain:

an antigenic composition including at least one antigen according to the invention, reagents necessary for carrying out the immunological reaction between the above-mentioned antigens and the antibodies possibly present in the biological sample, reagents making possible the detection of the antigen-antibody complex produced by the immunological reaction.

These reagents are for example labelled or capable of being recognized by a labelled reagent.

II—Isolation of the clone DG 210:

a) Construction of the Library

A DNA genomic bank was constructed in the expression bacteriophage λgt11 by using the genomic DNA of the clone Tak 9–96 of *P. falciparum* (ref. done Tak 9–96: Science 212, 137; 1981) in accordance with the protocol described in the detail in the EP patent application of Feb. 9, 1987 published under the number 0343186.

Briefly, the DNA was excised by DNAase I in the presence of Mn2+ions, methylated by EcoRI methylase to protect the natural EcoRI sites then repaired by the DNA polymerase of the T4 bacteriophage and the DNA ligase of EcoRI. EcoRI "linkers" (synthetic oligomers) were ligated to the DNA fragments of *P. falciparum* and the artifical sites thus added were released by cutting with the enzyme EcoRI The fragments were purified on a sucrose gradient and ligated to the DNA of the vector λgt11 suitably prepared (i.e. cut with EcoRI and dephosphorylated—sold by Promega Biotec). The DNA was encapsidated in vitro in viral particles. The bacteriophages derived from this procedure constitute a genomic DNA library.

b) Immunological Screening of the Bank

The technical details of screening are given in the text of the patent application 034186. Of a series of monoclonal antibodies (Mabs) used previously, Mab 245 (Soulier et al., *Revue Francaise de Transfusion et Immunohématologie*, Tome XXV, No. 4, 1982, page 373) of class IgM, a class of antibodies incapable of cooperating with the monocytes is the only one which has proved capable of entering into competition with the polyclonal antibodies of an immune subject active in the ADCI test, i.e. of appreciably reducing the inhibitory effect of these antibodies in ADCI, suggesting that the target epitope of these antibodies capable of cooperating with the monocytes and of this Mab 245 is identical. It is this antibody which was used for the isolation of the gene by screening of a band of genomic DNA cloned in the expression vector λgt11.

A direct screening by antigen/antibody reaction with the proteins synthesized by the clones of the library proved to be unsuccessful. Since this Mab is capable of entering into competition with other antibodies for a epitope bone by the parasite protein, another method of screening was then used.

The recombinant antigens were screened by a competition test using indirect immunofluorescence The monoclonal antibody Mab 243 in the presence of the merozoite was incubated with each of the recombinant antigens (supernatant of different clones of the genomic band) and the inhibition of the binding of the antibody to the parasite was measured by indirect immunofluorescence (technique described in H. BOUHAROUN-TAYOUN et al., 1990, J. Exp. Med. 172: 1633–1641).

Six antigens proved positive, i.e. inhibitory, and were studied in detail. These six protein antigens thus selected were bound to resins in order to effect affinity purifications of the poyclonal antibodies derived from immune human sera according to the technique described by OKAZI et al. These immunoglobulins thus purified were studied. Among the latter, the one obtained by binding to the protein synthesized by the done DG 210 recognizes in Western blot the 48 kD dimer which appears to be identical with that recognized by the cytophilic classes of IgG found in adult subjects in a state of clinical resistance to the disease and by the non-cytophilic classes of the sensitive individuals. On the other hand, it is different from the antigen MSA2, a surface antigen of the merozoite which on the same gene appears as a pciypeptide of higher molecular weight (Figures). The results of Table I show that the antibodies isolated by immunoaffinity to the protein secreted by the clone DG 210 are capable of promoting in vitro the inhibitory effect on the growth of the trophozoite induced by the manocytes by the ADCI procedure.

The clone DG 210 was deposited with the CNCM on Oct. 19, 1992 under the number No. I-1270.

Characterization of the Protein Synthesized by the Clone DG 210

The human antibodies immunoabsorbed on this protein like those produced in the mouse by immunization with the done DG 210 show in indirect fluorescence an image in clusters designating the circumference of the merozoites within the mature intra-erythrocytic schizonts. This indication that the molecule is localized at the membrane of the merozoites was confirmed on the one hand by extraction with a non-ionic detergent, Triton X114, from purified merozoites and detection of the protein in the soluble "detergent" phase on the other, by the action of phospholipase C of *Bacillus aureus*, this enzyme releasing the protein from a preparation of purified merozoites which thus indicates that the latter is anchored by a phosphatidyl-inositol group; finally, by revelation of the localization of the antibodies in electron microscopy with the aid of a second antibody labelled with colloidal gold: these antibodies are directed mainly against an antigen situated at the surface of the merozoites of *P. falciparum*.

These results confirm that the antigen capable of stimulating the antibody-dependent cytotoxicity mechanism (ADCI) is situated at the surface of the extracellular form of the parasite, the merozoite, In addition, the antibodies obtained by immunoaffinity on the recombinant product of the clone DG 210 have a very high inhibitory potency towards the growth of *P. falciparum* in the ADCI test whereas these same antibodies have no effect on the infection of the red cell by the merozoite The antibody controls prepared in the same manner with other control recombinant proteins including MSA2 and RESA had no inhibitory effect either directly or in the ADCI assays (Figure). The results are found in three separate experiments involving three different isolates of antibodies. Two of these results are shown in FIG. 1.

These results are confirmed by complementary observations. The isotypic distribution of the antibodies directed against the recombinant protein derived from the clone DG 210 exhibits the following characteristics. IgG2 isotypes are found much more abundantly in the unprotected patients whereas the protein is recognized preferentially by cytophilic IgG1 and IgG3 in the blood of protected subjects. Thus, the epitopes contained in the recombinant protein of the done DG 210 have all the desired characteristics for a protein with a vaccinating effect, namely that they might induce in vivo non-cytophilic antibodies in unprotected subjects which on the other hand, are cytophilic in protected subjects and thus are capable of inducing the ADCI reaction in vivo.

Finally, the study of the lymphoproliferative response of 70 subjects exposed to malaria (in Senegal and Madagascar) reveals that the peptides II, III and IV define epitopes recognized by the T lymphocytes.

A strong prevalence of lymphoproliferative responses (>50% of the population study) was observed in these subjects exposed to the disease.

Sequencing and Characterization of the Genome of the Clone DG 210

The genome of the done DG 210 has a length of 1300 base pairs. It was possible to determine its size by using the method described by McCutchan (McCutchan et al. (1984), Science 225: 625–627). Briefly, the genome is digested by the Mung bean endonuclease, the restriction fragments are then hybridized with the DG 210 probe labelled with phosphorus 32, and revealed in autoradiography according to procedures well-known to specialists skilled in the art.

The "North Blot" study of these same fragments and revealed by the same radioactive probe confirms that the gene is expressed during the erythrocytic phase of the cycle of the parasite.

The analysis of the sequence of 192 base pairs of the insert was carried out by the method of Sanger et al. (PNAS, 74: 5463, 1977), called "dideoxy-termination" method.

The invention also relates to the recombinant nucleic acids containing at least one of the polypeptide sequences I, II, III or IV or a combination of these as well as to the micro-organisms, in particular the E. coli bacteria, transformed by these recombinant nucleic acids and capable of expressing said polypeptide.

The invention relates to these nucleic acid sequences or equivalent sequences which can be synthesized and which code for the same amino acids.

It will be immediately apparent to the person skilled in the art that in these sequences some of the nucleotides may be replaced by others on account of the degeneracy of the genetic code without the encoded peptides being modified. All of these nucleotide sequences, as well as those which code for polypeptide which differ from the foregoing by one or more amino acids without their intrinsic immunogenic activity being similarly modified form part of the invention. Obviously the same holds for the nucleotide sequences which may be reconstituted and which are capable of coding for oligomers such as defined above The monomeric motifs are directly linked end-to-end or through the intermediary of peptide; sequences without effect on the immunogenic properties of the oligomers thus formed.

Finally, the invention relates to the vectors modified by these sequences, these vectors being naturally provided with regulatory and termination elements preceding and following the above-mentioned nucleic acid sequences which will permit the expression of these latter in competent cellular organisms.

Among the nucleotide sequences which code for the characteristic peptides which have been defined above, mention should be made of those which are characterized by the triplet sequences which follow (SEQ ID NO:5–8), these sequences corresponding in particular for the first to peptide I and for the three others to peptides II, III and IV whose formulae were indicated previously

```
CAT GAA AGG GCA AAA AAT GCT TAT CAA AAA      (1)
GCA AAC CAA GCT GTT TTA AAA GCA AAA GAA
GCT TCT AGT TAT GAT TAT ATT TTA GGT TGG
GAA TTT GGA GGA GGC GTT CCA GAA CAC AAA
AAA GAA GAA AAT ATG TTA TCA CAT TTA TAT
GTT TCT TCA AAG GAT AAG GAA AAT ATA TCT
AAG GAA AAT GAG
CAT GAA AGG GCA AAA AAT GCT TAT CAA AAA      (2)
GCA AAC CAA GCT GTT TTA AAA GCA AAA GAA
GCT TCT AGT TAT GAT
```

-continued

```
GCA AAA GAA GCT TCT AGT TAT GAT TAT ATT      (3)
TTA GGT TGG GAA TTT GGA GGA GGC GTT CCA
GAA CAC AAA AAA GAA GAA AAT
CCA GAA CAC AAA AAA GAA GAA AAT ATG TTA      (4)
TCA CAT TTA TAT GTT TCT TCA AAG GAT AAG
GAA AAT ATA TCT AAG GAA AAT GAG
```

Bacteria harbouring the above-mentioned clones DG 210 were deposited with the Collection Nationale des Cultures de Microorganismes (CNCM) at the Pasteur Institute in Paris on Oct. 19, 1992 under the number I-1270.

The object of the invention is also DNA or RNA primers utilizable for example in the framework of the synthesis of nucleotide sequences, possibly flowed by polypeptide synthesis, according to the invention by the PCR (Polymerase Chain Reaction) procedure such as described in the American patents Nos. 4683212 and 4683195 and the European patent application No. 200362. A description of the procedure used here is found in the PCT patent application No. FR 91/00639, pages 28 to 30.

The peptides of the invention can also be prepared by the standard procedures used in the field of peptide synthesis. This synthesis may be carried out in homogeneous solution or on a solid phase such as described above by the procedures described in HOUBENWEYL or MERRIFIELD.

III—Study of the Polymorphism of the Gene and Epitopes Defined by the Clone DG 210

A major impediment to the production of an effective vaccine is, in addition to the complexity of the cycle of the parasite, its antigenic diversity and the high degree of polymorphism from one strain to another.

The conservation of the gene and defined epitopes in the clone DG 210 has been studied by several procedures in a series of isolates of plasmodiae.

By using the following nucleotides as primers: (SEQ ID NO:9–10)

GAA AGG GCA AS A AAT GCT TAT (5)

or TAA AAG GAA TCT ATA TAA AAG (6)

the DNA fragments of two cultures o cultured strains of African P. falciparum, of 4 Thai isolates and 29 African isolates could be amplified by the PCR procedure.

The corresponding gene was present everywhere, with no apparent size polymorphism whereas a similar experiment using the same PCR procedure with primers of the MSA1 and MSA2 regions could not demonstrate this result.

Similarly, the screening of the proteins and peptides by Western blot prepared from 6 Thai or African isolates with antibodies purified using an affinity column with the peptide 210 as ligand have enabled the 48 kD dimer to be revealed in all the variants, with no change of molecular weight from one isolate to another.

Finally, 10 isolates from the Congo were studied by means of indirect immunofluorescence by the same procedure as above and were all positive, and all the parasites of each of the isolates were labelled with the antibodies purified by affinity.

Everything thus seems to point to the absence of antigenic polymorphism at least in the region of the molecule bearing the epitope B. just like the conservation of the size of this protein from one isolate to another.

These results confirm those obtained in ADCI, and more particularly in the competition tests in which the non-cytophilic antibodies obtained after an initial attack by the parasite are excellent competitors of the cytophilic antibodies of the protected adults.

In as much as the non-cytophilic antibodies obtained after the initial attack correspond to a single isolate, and the protected adults are protected against the infection of a large number of polymorphic isolates (which, furthermore, were isolated in the competition experiments), it is right to conclude that the epitopes concerned in the competition experiments are representative of non-polymorphic, conserved regions.

The polypeptides and proteins of the invention are hence characterized by a broad activity spectrum as vaccinating composition.

What is claimed is:

1. An isolated DNA coding for a protein or peptide which is recognized by cytophilic antibodies of protected subjects (by premonition) against infection by the Plasmodia and recognized by non-cytophilic antibodies of subjects sensitive to the infection by the Plasmodia, wherein said cytophilic antibodies recognizing said protein or peptide inhibit the growth of the Plasmodia in an antibody-dependent cellular inhibition test (ADCI), and wherein said protein or peptide comprises SEQ ID NO:1.

2. An isolated DNA coding for a protein having a molecular weight of 48,000 daltons +/−10% and which is a surface protein of the merozoite of Plasmodium falciparum which is recognized by cytophilic antibodies of protected subjects (by premonition) against infection by the Plasmodia and recognized by non-cytophilic antibodies of subjects sensitive to the infection by the Plasmodia, wherein said cytophilic antibodies recognizing said protein or peptide inhibit the growth of the Plasmodia in an antibody-dependent cellular inhibition test (ADCI), and wherein the protein comprises a sequence selected from the group consisting of SEQ ID NO:2 SEQ ID NO:3, and SEQ ID NO:4.

3. An isolated nucleotide sequence comprising SEQ ID NO: 5.

4. An isolated nucleotide sequence which induces the synthesis of a peptide exhibiting an antigen cross-reaction with the protein of 48,000 daltons of the merozoites of *Plasmodium falciparum*, and which is selected from the group consisting of SEQ ID NO: 6, SEQ ID NO: 7, and SEQ ID NO: 8.

5. A recombinant DNA comprising the DNA of claim 3.

6. A recombinant DNA comprising at least one DNA of claim 4.

7. A recombinant cloning vector, comprising the nucleotide sequence of claim 3.

8. A recombinant cloning vector, comprising the nucleotide sequence of claim 4.

9. The recombinant cloning vector of claim 7, wherein the nucleotide sequence is under the control of a promoter and regulatory elements homologous or heterologous vis-a-vis a host cell, for expression in the host cell.

10. The recombinant cloning vector of claim 8, wherein the nucleotide sequence is under the control of a promoter and regulatory elements homologous or heterologous vis-a-vis a host cell, for expression in the host cell.

11. A recombinant expression vector, comprising the nucleotide sequence of claim 3.

12. A recombinant expression vector, comprising the nucleotide sequence of claim 4.

13. The recombinant expression vector of claim 11, wherein the nucleotide sequence is under the control of a promoter and regulatory elements homologous or heterologous vis-a-vis a host cell, for expression in the host cell.

14. The recombinant expression vector of claim 12, wherein the nucleotide sequence is under the control of a promoter and regulatory elements homologous or heterologous vis-a-vis a host cell, for expression in the host cell.

15. A recombinant host cell, which is transformed by the vector of claim 9 or claim 13.

16. The host cell of claim 15, which is selected from the group consisting of a bacterium, a yeast, an insect cell, and a mammalian cell.

17. The host cell of claim 16, which is an *E. coli* cell or a CHO cell.

18. A recombinant host cell, which is transformed by the vector of claim 10 or claim 14.

19. The host cell of claim 18, which is selected from the group consisting of a bacterium, a yeast, an insect cell, and a mammalian cell.

20. The host cell of claim 19, which is an *E. coli* cell or a CHO cell.

21. A recombinant expression vector, comprising the nucleotide sequence of claim 1.

* * * * *